US006216537B1

(12) United States Patent
Henschel et al.

(10) Patent No.: US 6,216,537 B1
(45) Date of Patent: Apr. 17, 2001

(54) ACCELEROMETER FOR IMPLANTABLE MEDICAL DEVICE

(75) Inventors: Mark E. Henschel, Phoenix; David Brian Hall, Chandler; Scott B. Sleeper, Phoenix; Lary R. Larson, Gold Canyon; Brian S. Child; Patrick F. Malone, both of Phoenix; Samuel F. Haq; David A. Ruben, both of Mesa; Joan A. O'Gara; James E. Volmering, both of Phoenix, all of AZ (US); Roy L. Inman, Corning, NY (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/282,485

(22) Filed: Mar. 31, 1999

(51) Int. Cl.[7] .............................. G01P 1/02; A61N 1/365
(52) U.S. Cl. .................................. 73/493; 607/17; 607/18
(58) Field of Search .......................... 73/493, 431, 514.15, 73/514.16, 514.21, 514.36, 514.38; 607/17, 18, 19, 21, 22, 24, 27

(56) References Cited

U.S. PATENT DOCUMENTS

| 4,140,132 | 2/1979 | Dahl . |
| 4,379,459 | 4/1983 | Stein . |
| 4,476,868 | 10/1984 | Thompson . |
| 4,556,063 | 12/1985 | Thompson et al. . |

(List continued on next page.)

FOREIGN PATENT DOCUMENTS

| 86 26 133 U | 6/1988 | (DE) . |
| 0 434 878 A1 | 7/1991 | (EP) . |
| 0 529 122 A1 | 3/1993 | (EP) . |
| WO 91/13364 | 9/1991 | (WO) . |
| WO 95/02431 | 1/1995 | (WO) . |
| WO 95/03086 | 2/1995 | (WO) . |

OTHER PUBLICATIONS de Bruin et al., "Two–Chip Smart Accelerometer", *EG&G IC Sensors*, Technical Paper; Milpitas, California, pp. 1–4 (Undated).
Eg & G IC Sensors, Application Note, Model 3255 Accelerometer, Note TN–010, pp. 1–8 (Apr. 1995).
Roylance et al., "A Batch–Fabricated Silicon Accelermeter", *IEEE Trans. Electron Devices*, 26(12) pp. 1911–1917 (1979).
VTI Hamlin, "Silicon Capacitive Sensor Technology" http://www.vti.fi/Products/Technology.html, accessed Feb. 10, 1999.

Primary Examiner—Helen C. Kwok
(74) Attorney, Agent, or Firm—Thomas F. Woods; Harold R. Patton; Girma Wolde-Michael

(57) ABSTRACT

An accelerometer device which can be mounted on a substrate, e.g., a circuit board enclosed in a medical device, includes an accelerometer sensing element having an axis of sensitivity and further includes first and second multilayer end caps. The substrate generally defines a mounting plane. The accelerometer sensing element includes a device body having a longitudinal axis extending between generally parallel first and second ends thereof and further includes a principal surface extending between the first and second ends of the device body parallel to the longitudinal axis. The axis of sensitivity of the sensing element is generally perpendicular to a plane defined by the principal surface. Further, the accelerometer sensing element includes conductive pad regions on each of the first and second ends of the device body. Each of the first and second multilayer end caps includes conductive elements on one side thereof and further includes conductive traces electrically connected to the conductive elements thereof. Each of the conductive traces of the first and second multilayer end caps terminate at a surface mount contact region along at least one edge thereof. The first and second multilayer end caps are attached to the first and second ends of the device body such that, when the accelerometer device is mounted on a substrate, the axis of sensitivity of the accelerometer sensing element is perpendicular to the mounting plane defined thereby.

60 Claims, 5 Drawing Sheets

U.S. PATENT DOCUMENTS

| | | |
|---|---|---|
| 4,653,326 | 3/1987 | Danel et al. . |
| 4,679,434 | 7/1987 | Stewart . |
| 4,742,182 | 5/1988 | Fuchs . |
| 4,821,723 | 4/1989 | Baker et al. . |
| 4,891,985 | 1/1990 | Glenn . |
| 4,896,068 | 1/1990 | Nilsson . |
| 4,987,781 | 1/1991 | Reimann . |
| 5,014,702 | 5/1991 | Alt . |
| 5,031,615 | 7/1991 | Alt . |
| 5,044,366 | 9/1991 | Alt . |
| 5,127,404 | 7/1992 | Wyborny et al. . |
| 5,131,388 | 7/1992 | Pless . |
| 5,144,949 | 9/1992 | Olson et al. . |
| 5,158,078 | 10/1992 | Bennett et al. . |
| 5,199,428 | 4/1993 | Obel et al. . |
| 5,207,218 | 5/1993 | Carpentier et al. . |
| 5,215,084 | 6/1993 | Schaldach . |
| 5,235,237 | 8/1993 | Leonhardt . |
| 5,312,453 | 5/1994 | Shelton et al. . |
| 5,314,430 | 5/1994 | Bardy . |
| 5,315,205 | 5/1994 | Ohno et al. . |
| 5,318,596 | 6/1994 | Barreras et al. . |
| 5,330,507 | 7/1994 | Schwartz . |
| 5,331,966 | 7/1994 | Bennett et al. . |
| 5,354,316 | 10/1994 | Keimel . |
| 5,373,267 | 12/1994 | Kaida et al. . |
| 5,425,750 | 6/1995 | Moberg . |
| 5,503,016 | 4/1996 | Koen . |
| 5,545,186 | 8/1996 | Olson et al. . |
| 5,594,172 | 1/1997 | Shinohara . |
| 5,616,863 | 4/1997 | Koen . |
| 5,674,258 | 10/1997 | Henschel et al. . |
| 5,745,347 | 4/1998 | Miller et al. . |
| 5,885,471 | 3/1999 | Rubeu et al. . |

ACCELEROMETER FOR IMPLANTABLE MEDICAL DEVICE

FIELD OF THE INVENTION

The present invention relates generally to accelerometers. More particularly, the present invention relates to structure for mounting accelerometers.

BACKGROUND OF THE INVENTION

Accelerometers are well known in the art. An accelerometer is a device which measures acceleration, or more accurately measures force exerted by a body as a result of a change in the velocity of the body. A moving body possesses an inertia which tends to resist change in velocity. It is this resistance to change in velocity that is the source of the force exerted by the moving body. This force is directly proportional to the acceleration component in the direction of movement when the moving body is accelerated.

Various types of accelerometers are available. Generally, in a micromachined accelerometer formed using silicon, a central (e.g., typically spherical or rectangular shaped) mass is suspended by one or more microbridges. The microbridges are attached to a supporting substrate which surrounds the mass with a gap provided therebetween. The mass is supported within and has free movement relative to the supporting structure.

The movement of the mass is measured in various manners. For example, the movement of the mass may be measured by measuring a corresponding change in the output of a wheatstone bridge incorporating beam piezo resistors formed in the microbridges.

Further, for example, in silicon capacitive accelerometers, such as those available from VTI Hamlin (Finland), the sensing element of the accelerometer consists of three layers of silicon isolated from each by thin glass layers. The middle silicon layer incorporates a cantilevered mass beam structure. The force of gravity or acceleration acting on the silicon mass causes the beam structure to bend. This deflection is detected as a change in the distance between electrodes in capacitors formed on both sides of the mass using metal electrodes.

Generally, such micromachined accelerometers require external circuitry to process the signal output by the accelerometer. For example, such a signal output may be used for triggering an automobile airbag of an airbag deployment system, may be used for triggering medical treatment in an implantable medical device, or may be used as an input for any other application where acceleration is to be detected.

Accelerometers are generally constrained in that typically a micromachined accelerometer as described above has a single axis sensitive to acceleration. That is, the sensing element of an accelerometer can only measure acceleration along a line perpendicular to a particular plane thereof. For example, the plane may be defined by a principle surface of the sensing element from which side during fabrication various fabrication steps are performed, e.g., masking, etching, etc. For example, in an automobile airbag system, the direction of acceleration which must be sensed in the event of a collision is typically along a line lying in a horizontal plane, i.e., parallel to the ground. Further, for example, the direction of acceleration which is to be sensed of a person implanted with an implantable medical device, may be the direction of acceleration along a line lying in a horizontal plane, i.e., a line orthogonal to a plane defined by the patient's chest.

Various accelerometer structures are available such that the accelerometer can be surface mounted on a substrate in one or more orientations. For example, an accelerometer available from EG&G Inc., (Wellesley, Mass.), available under the Model No. 3255 includes an accelerometer wherein the sensitive axis is perpendicular to the bottom plane of the package. The package can be mounted in two orientations, allowing the sensitive axis to be either perpendicular or parallel to the mounting plane defined by the substrate upon which it is mounted. This accelerometer measures acceleration using a wheatstone bridge technique.

Table 1 below lists U.S. Patents showing other transducer, e.g., accelerometer, configurations.

TABLE 1

| U.S. Pat. No. | Inventor(s) | Issue Date |
| --- | --- | --- |
| 4,896,068 | Nilsson | 23 January 1990 |
| 5,044,366 | Alt | 3 September 1991 |
| 5,215,084 | Schaldach | 1 June 1993 |
| 5,425,750 | Moberg | 20 June 1995 |
| 5,674,258 | Henschel et al. | 7 October 1997 |
| 5,373,267 | Kaida et al. | 13 December 1994 |
| 5,318,596 | Barreras et al. | 7 June 1994 |
| 5,031,615 | Alt | 16 July 1991 |
| 4,653,326 | Danel et al. | 31 March 1987 |
| 5,594,172 | Shinohara | 14 January 1997 |
| 4,140,132 | Dahl | 20 February 1997 |
| 4,679,434 | Stewart | 14 July 1987 |
| 4,742,182 | Fuchs | 3 May 1988 |
| 4,891,985 | Glenn | 9 January 1990 |
| 4,987,7810 | Reimann | 29 January 1991 |
| 5,014,702 | Alt | 14 May 1991 |
| 5,031,615 | Alt | 16 July 1991 |
| 5,235,237 | Leonhardt | 10 August 1993 |
| 5,745,347 | Miller et al. | 28 April 1998 |
| 5,616,863 | Koen | 1 April 1997 |
| 5,503,016 | Koen | 2 April 1996 |

All references listed in Table 1, and references listed elsewhere herein, are incorporated by reference in their respective entireties. As those of ordinary skill in the art will appreciate readily upon reading the Summary of the Invention, Detailed Description of the Embodiments, and claims set forth below, at least some of the devices and methods disclosed in the references of Table 1, and elsewhere herein, may be modified advantageously by using the teachings of the present invention. However, the listing of any such references in Table 1, or elsewhere herein, is by no means an indication that such references are prior art to the present invention.

SUMMARY OF THE INVENTION

The present invention has certain objects. That is, various embodiments of the present invention provide solutions to one or more problems existing in the prior art with respect to the mounting of accelerometer devices, such as for mounting accelerometers in implantable medical device applications. One of such problems involves the need to rotate the axis of sensitivity of many accelerometer devices 90° when mounted on a substrate as compared to conventional mounting of such devices. Further, for example, other problems include: the need to place the accelerometer device relative to the circuit board in a predetermined orientation, the inability to effectively mass produce such accelerometer devices, the inability to test accelerometer devices after assembly, and the inability to provide a small, compact, and robust package.

In comparison to known techniques for providing surface mountable accelerometer devices and assemblies, such as for implantable medical devices, various embodiments of the present invention may provide one or more of the following advantages. For example, the present invention provides for desired orientation of the axis of sensitivity of the accelerometer device in a desired application. Further, embodiments of the present invention provide for the ability to mount the accelerometer 1800 in two axes while still maintaining functionality. Yet further, the various embodiments of the present invention may provide for the advantages of effective mass production, testability after assembly, and provision of a small, compact, and robust package for use in various applications, such as implantable medical devices.

Some embodiments of the present invention include one or more of the following features: a surface mountable accelerometer device for use in an implantable medical device; an accelerometer sensing element having an axis of sensitivity; at least one interposer, e.g., a multilayer end cap, for use in mounting a transducer element, e.g., an accelerometer sensing element, such that an axis of sensitivity of the transducer element is in a particular orientation; an accelerometer sensing element which includes a device body having a longitudinal axis extending between generally parallel first and second ends thereof, a principal surface that extends between the first and second ends of the device body parallel to the longitudinal axis with the axis of sensitivity being perpendicular to a plane defined by the principle surface, and two or more conductive pad regions on each of the first and second ends of the device body; first and second multilayer end caps for use in mounting an accelerometer sensing element to a substrate such that the axis of sensitivity of the accelerometer sensing element is generally rotated 90° when mounted relative to the possible orientation of the axis of sensitivity if the end caps are not used; and first and second multilayer end caps which each include generally parallel first and second sides, conductive elements on the first side of the end caps for electrical connection to conductive pad regions of a sensing element, and conductive traces on the second side electrically connected to the conductive elements and which terminate in surface mount contact regions along an edge of the multilayer end caps for use in mounting the accelerometer sensing element to a substrate.

Further, some embodiments of the present invention include one or more of the following features: first and second multilayer end caps which each include surface mount contact regions along first and second edges thereof such that the sensing element can be mounted 180° in two axes while maintaining functionality; a capacitive sensing element with one or more electrodes lying in corresponding planes generally parallel to the principle surface of element with the axis of sensitivity being generally perpendicular to the electrodes; an accelerometer sensing element having first and second ends with conductive pads being symmetrically distributed thereon; an implantable medical device having a housing in which the accelerometer device is enclosed; an accelerometer assembly generally including a substrate (e.g., circuit board) defining a mounting plane, an accelerometer sensing element, and first and second multilayer end caps including two or more conductive traces terminating at surface mount contact regions along edges thereof for electrical connection to two or more surface mount contact pads of the substrate such that the axis of sensitivity of the accelerometer sensing element is perpendicular to the mounting plane defined by the substrate; and a transducer assembly including a substrate (e.g., circuit board) defining a mounting plane, a sensing element having an axis of sensitivity, and at least one interposer element for connecting the sensing element to the substrate such that the axis of sensitivity of the accelerometer sensing element is perpendicular to the mounting plane defined by the substrate.

Yet further, some embodiments of the present invention may include one or more of the following features: attaching first and second multilayer end caps to first and second ends of a device body, respectively, with conductive elements of the first and second multilayer end caps in electrical contact with conductive pad regions of the first and second ends of the device body; mounting an accelerometer device on a substrate (e.g., printed circuit board) with surface mount contact regions thereof electrically connected to surface mount contact pads of the substrate such that the axis of sensitivity of the accelerometer sensing element is perpendicular to a mounting plane defined by the substrate; providing an accelerometer sensing element having an axis of sensitivity and a first and second multilayer end cap and thereafter attaching the first and second multilayer end caps to first and second ends of a device body of the accelerometer sensing element such that surface mount contact regions along an edge of the first and second end caps lie in a plane defined by a principle surface of the accelerometer sensing element; attaching an interposer element to at least one of a first and second end of a device body of an accelerometer sensing element with the interposer element including at least two surface mount contact regions with at least a portion of the surface mount contact regions lying in a plane defined by a principle surface of the accelerometer sensing element; and enclosing an accelerometer device in an implantable medical device housing.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

DETAILED DESCRIPTION OF THE EMBODIMENTS

In accordance with the present invention, a surface mountable accelerometer device is formed which may be useable in a variety of applications. For example, the accelerometer devices formed herein may be used in any electronic apparatus for a variety of applications, e.g., airbag deployment. The present invention is particularly beneficial for use in implantable medical devices.

Figure 1:
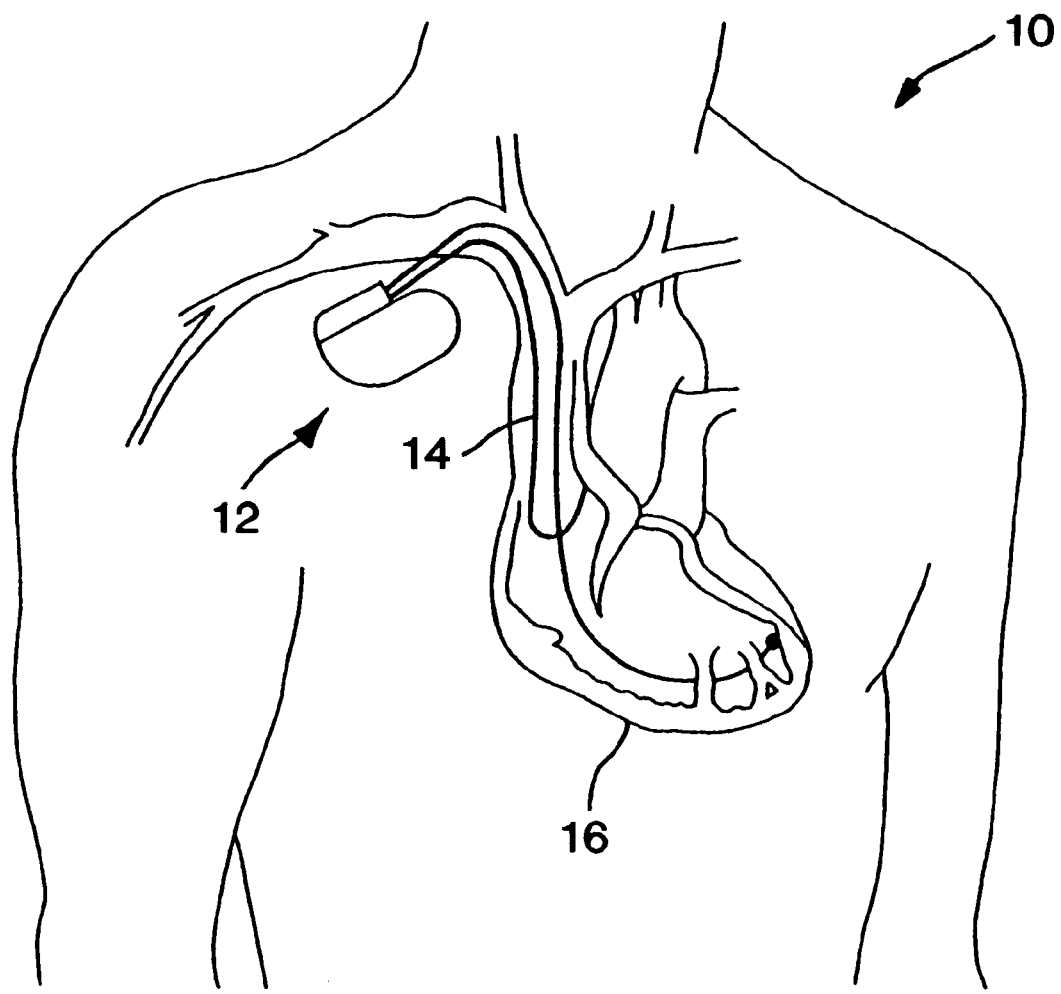
FIG. 1 is a diagram illustrating an implantable medical device in a body; the implantable medical device including a surface mountable accelerometer device according to the present invention.

FIG. 1 is a simplified schematic view of an implantable medical device 12 including a surface mountable accelerometer device according to the present invention implanted in a body 10 near a human heart 16. Implanted medical device 12 is electrically connected to the heart by one or more leads 14. In the case where the implanted medical device 12 is a pacemaker, the leads 14 are pacing and sensing leads connected to heart 16 from the implantable medical device 12. Such leads sense electrical signals attendant to the depolarization and repolarization of the heart 16 and providing pacing pulses for causing depolarization of cardiac tissue in the vicinity of the distal ends thereof. Implantable medical device 12 may be any implantable cardiac pacemaker such as those disclosed in U.S. Pat. No. 5,158,078 to Bennett et al., U.S. Pat. No. 5,312,453 to Shelton et al., or U.S. Pat. No. 5,144,949 to Olson et al.

Implantable medical device 12 may also be a pacemaker-cardioverter-defibrillator (PCD) corresponding to any of the various commercially-available implantable PCDs. For example, the present invention may be practiced in conjunction with PCDs such as those described in U.S. Pat. No. 5,545,186 to Olson et al.; U.S. Pat. No. 5,354,316 to Keimel; U.S. Pat. No. 5,314,430 to Bardy; U.S. Pat. No. 5,131,388 to Pless; or U.S. Pat. No. 4,821,723 to Baker, et al.

Alternatively, implantable medical device 12 may be an implantable nerve stimulator or muscle stimulator such as that disclosed in U.S. Pat. No. 5,199,428 to Obel et al.; U.S. Pat. No. 5,207,218 to Carpentier, et al.; U.S. Pat. No. 5,330,507 to Schwartz; or an implantable monitoring device such as that disclosed in U.S. Pat. No. 5,331,966 issued to Bennett et al.

Further, for example, the implanted device 12 may be a defibrillator, a cardioverter-defibrillator, a brain stimulator, a gastric stimulator, a drug pump, a hemodynamic monitoring device, or any other implantable device that would benefit from a surface mounted accelerometer as described herein. Therefore, the present invention is believed to find wide application in any form of implantable medical device. As such, a description herein making reference to any particular medical device is not to be taken as a limitation of the type of medical device which can use a surface mountable accelerometer device as described herein.

Further, although the present invention is particularly described with reference to use in implantable medical devices, the present invention is in no manner limited to such applications. For example, the present invention may be used in any electronic application where a surface mountable accelerometer device as described herein is beneficial as would be readily apparent to one skilled in the art from the description herein. For example, the device as described herein may be used in automobile applications such as in air bag deployment mechanisms.

In general, the implantable medical device 12 may include a hermetically sealed enclosure that may include various elements such as an electrochemical cell (e.g., a lithium battery), circuitry that controls device operations and records rhythmic EGM episodes, telemetry transceiver antenna and circuit that receives downlinked telemetry commands from and transmits stored data in a telemetry uplink to an external programmer, etc. Generally, the medical device is implemented with a microprocessor-based architecture. However, electronic features and operations of the implantable medical device may be implemented in discrete logic or as a microcomputer-based system, as would be readily apparent to one skilled in the art from the description herein.

Figure 2:
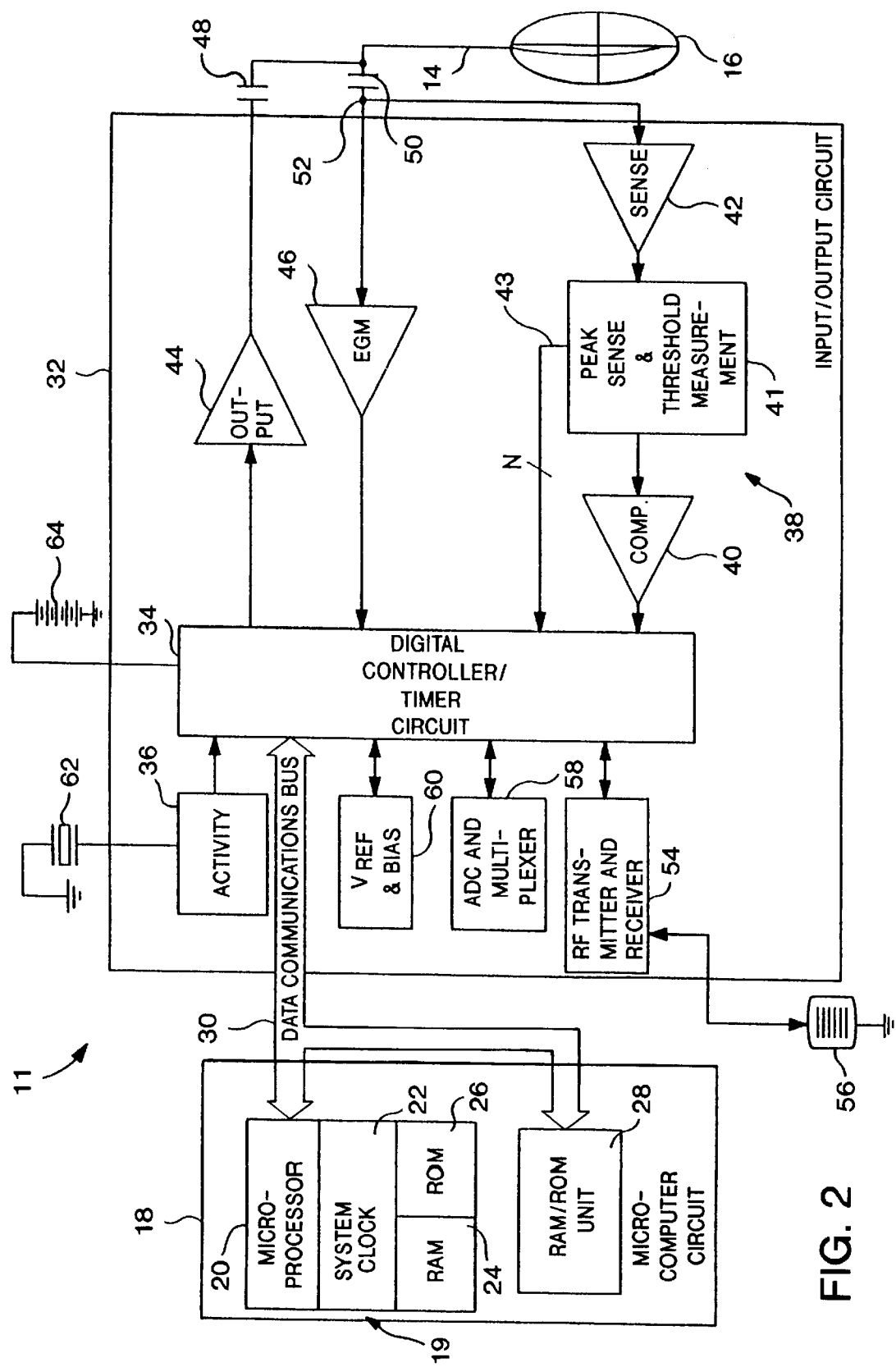
FIG. 2 is a general block diagram of the circuitry of one embodiment of an implantable medical device including a surface mountable accelerometer device according to the present invention.

FIG. 2 shows a block diagram illustrating components of a pacemaker 11 in accordance with one embodiment of the present invention where pacemaker 11 includes at least one surface mountable accelerometer device, e.g., activity sensor 62, according to the present invention. In the illustrative embodiment shown in FIG. 2, the pacemaker 11 is preferably programmable by means of an external programming unit (not shown). One such programmer suitable for the purposes of the present invention is the commercially-available Medtronic Model 9790 programmer. The programmer is a microprocessor device which provides a series of encoded signals to pacemaker 11 by means of a programming head which transmits radiofrequency (RF) encoded signals to pacemaker 11 according to a telemetry system such as, for example, that described in U.S. Pat. No. 5,127,404 to Wybomy et al. It is to be understood, however, that any programming methodology may be employed so long as the desired information is transmitted to and from the pacemaker 11.

Pacemaker 11 illustratively shown in FIG. 2 is electrically coupled to the patient's heart 16 by lead 14. Lead 14 is coupled to a node 52 in the circuitry of pacemaker 11 through input capacitor 50. In the presently disclosed embodiment, an activity sensor 62 provides a sensor output to an activity circuit 36 of input/output circuit 32. The activity sensor 62 is preferably a surface mountable accelerometer device according to the present invention. The surface mountable accelerometer is generally mounted on a printed circuit board with other pacemaker circuitry. When implanted, the circuit board is generally orthogonal to the ground when a patient having the implant is in an upright position. In other words, the axis of sensitivity of the accelerometer preferably runs into or out of the patients' chest. Input/output circuit 32 also contains circuits for interfacing to heart 16, antenna 56, and contains circuits 44 for application of stimulating pulses to heart 16 to control its rate under control of software-implemented algorithms in microcomputer unit 18.

Microcomputer unit 18 preferably comprises on-board circuit 19 that includes microprocessor 20, system clock 22, and on-board random access memory (RAM) 24 and read-only memory (ROM) 26. In this illustrative embodiment, off-board circuit 28 comprises a RAM/ROM unit. On-board circuit 19 and off-board circuit 28 are each coupled by a communication bus 30 to digital controller/timer circuit 34.

The electrical components shown in FIG. 2 are powered by an appropriate implantable battery power source 64 in accordance with common practice in the art. For the sake of clarity, the coupling of battery power to the various components of pacemaker 11 is not shown in the figures.

Antenna 56 is connected to input/output circuit 32 to permit uplinked/downlinked telemetry through RF transmitter and receiver unit 54. For example, unit 54 may correspond to the telemetry and program logic disclosed in U.S. Pat. No. 4,556,063 issued to Thompson et al., or to that disclosed in the above-referenced Wybomy et al. patent.

$V_{REF}$ and bias circuit 60 generates a stable voltage reference and bias currents for circuits of input/output circuit 32. Analog to digital converter (ADC) and multiplexer unit 58 digitizes analog signals and voltages to provide "real-time" telemetry intracardiac signals and battery end-of-life (EOL) replacement function.

Operating commands for controlling the timing of pacemaker 11 are coupled by bus 30 to digital controller/timer circuit 34, where digital timers and counters establish the overall escape interval of the pacemaker as well as various refractory, blanking, and other timing windows for controlling the operation of the peripheral components disclosed within input/output circuit 32. Digital controller/timer circuit 34 is preferably coupled to sense circuitry 38, including sense amplifier 42, peak sense and threshold measurement unit 41, and comparator/threshold detector 40. Sense amplifier 42 amplifies sensed electrocardiac signals and provides an amplified signal to peak sense and threshold measurement circuitry 41. Circuitry 41 in turn provides an indication of peak sensed voltages and measured sense amplifier threshold voltages on path 43 to digital controller/timer circuit 34. Sensed amplifier signals are also provided to comparator/threshold detector 40. Sense amplifier 42 may correspond to that disclosed in U.S. Pat. No. 4,379,459 to Stein.

Circuit 34 is further preferably coupled to electrogram (EGM) amplifier 46 for receiving amplified process signals sensed by an electrode disposed on lead 14. The electrogram signal provided by EGM amplifier 46 is employed when the implanted device is being interrogated by an external programmer (not shown) to transmit by uplinked telemetry a representation of an analog electrogram of the patient's electrical heart activity. Such functionality is, for example, shown in U.S. Pat. No. 4,556,063 to Thompson et al.

Output pulse generator 44 provides pulsing stimuli to the patient's heart 16 through coupling capacitor 48 in response to a pacing trigger signal provided by digital controller/timer circuit 34. Output amplifier 44, for example, may correspond generally to the output amplifier disclosed in U.S. Pat. No. 4,476,868 to Thompson.

Figure 3:
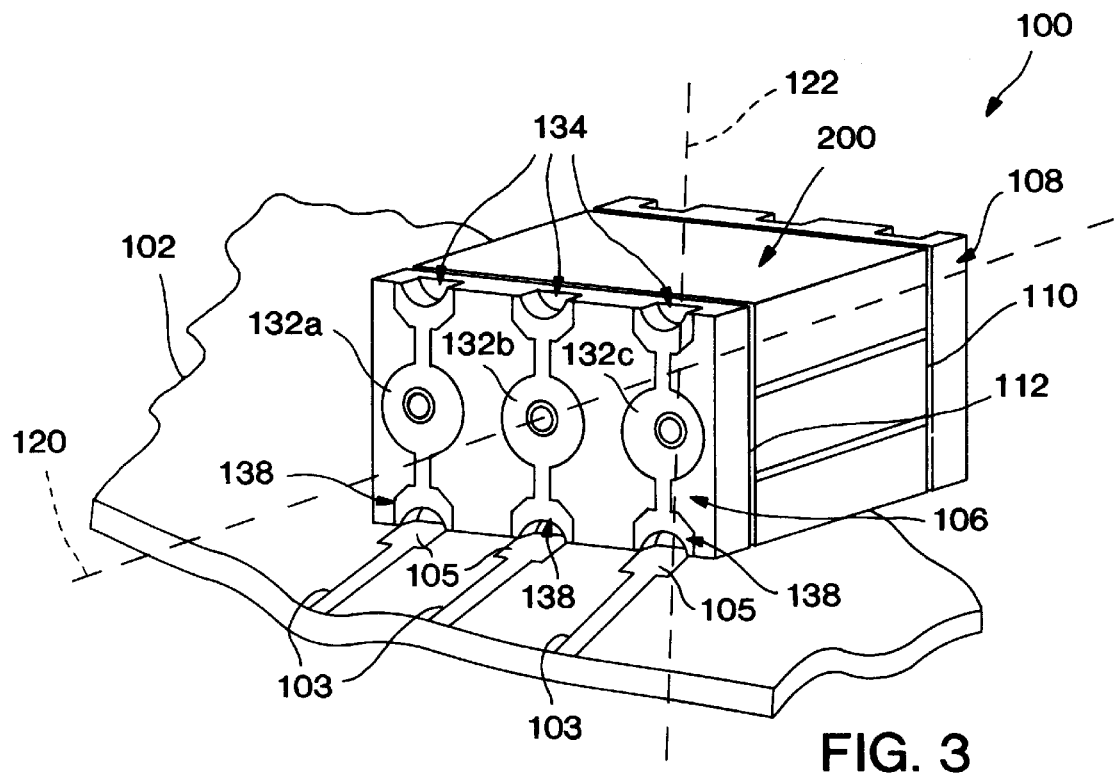
FIG. 3 is a perspective view of an illustrative embodiment of a surface mountable accelerometer device on a substrate according to the present invention.

FIG. 3 illustrates a surface mountable accelerometer device 100 according to the present invention. The surface mountable accelerometer device 100 is positioned relative to substrate 102 resulting in an accelerometer assembly. As used herein, substrate may refer to any material upon which accelerometer device 100 is mounted, attached, or otherwise electrically connected. For example, the substrate 102 may be a printed circuit board, such as that shown in FIG. 3, including metallization 103, such as surface mount contact pads 105, for electrical connection to the accelerometer device 100. Further, for example, the substrate 102 may be a ceramic substrate upon which the accelerometer device 100 is mounted. The substrate 102 defines a mounting plane on which the accelerometer device 100 is mounted.

Figure 7:
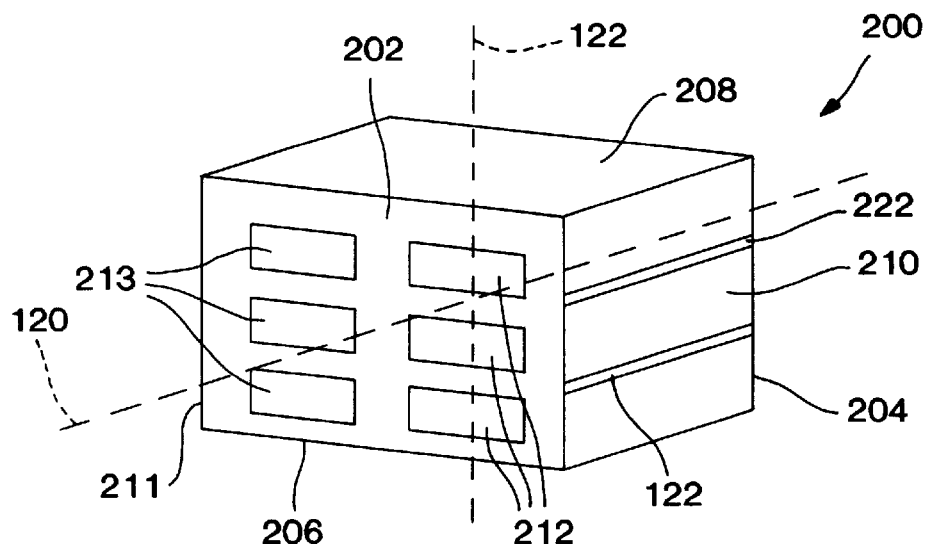
FIG. 7 is a perspective view of the accelerometer sensing element of the accelerometer device of FIG. 3.
Figure 8:
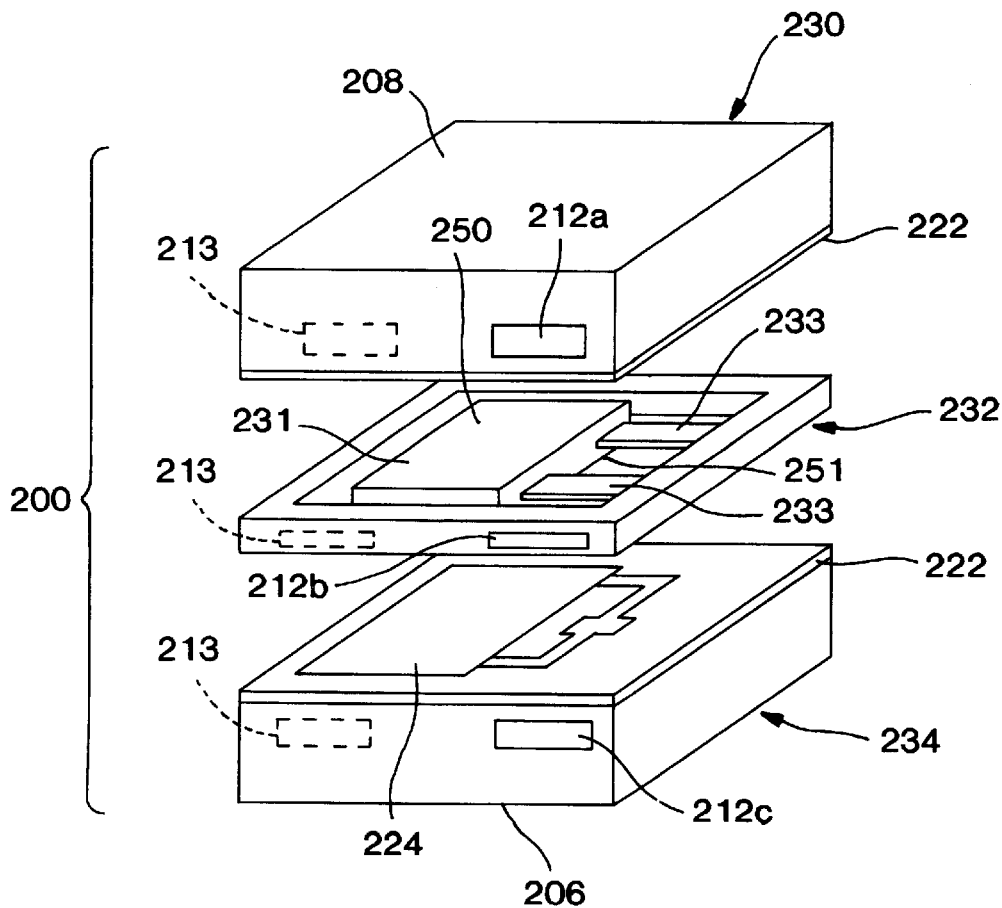
FIG. 8 is an exploded perspective view of the accelerometer sensing element of FIG. 7.

The surface mountable accelerometer device 100 as shown in FIG. 3 includes an accelerometer sensing element 200 as further shown in detail in FIGS. 7 and 8. Further, the surface mountable accelerometer device 100 includes first and second multilayer end caps 106, 108 which are attached to accelerometer sensing element 200 for mounting the sensing element 200 on the substrate.

As shown and described further below, first and second multilayer end caps 106, 108 are interposed between conductive pad regions of accelerometer sensing element 200 and metallization on substrate 102. As such, these end caps 106, 108 may also be referred to as interposers. First and second multilayer end caps 106,108 are one illustrative embodiment of an interposer according to the present invention which rotates the attachment of an accelerometer sensing element 900 relative to the mounting of such a sensing element without the interposer. Any interposer which provides the advantages of rotating attachment of an accelerometer sensing element 90° from that which would be possible without the interposer may be used advantageously according to the present invention.

FIGS. 7 and 8 illustrate formed and exploded views, respectively, of one embodiment of an accelerometer sensing element 200. The accelerometer sensing element 200, a capacitive type sensing element, generally includes three layers of silicon 230, 232, and 234 isolated from each other by thin glass layers 222. The middle silicon layer incorporates a cantilevered mass beam structure 231. The mass beam structure 231 is supported by bridges 233 connected to middle silicon layer 232. Mass beam structure 231 includes conductive electrodes 250, 251 formed on both sides of the mass beam structure 231. The lower silicon layer 234 includes a conductive electrode 224 formed thereon and, likewise, upper silicon layer 230 includes a conductive electrode (not shown) corresponding to the conductive electrode 224.

In operation, the force of gravity or acceleration acting on the accelerometer sensing element 200 causes the mass beam structure 231 to bend. As such, the mass beam structure deflection can be detected as a change in the distance between the electrodes 224 and 251, and between the electrode 250 and the conductive electrode (not shown) formed on silicon layer 230. Contacts for the electrodes to provide an output signal external to the accelerometer sensing element 200 are provided by means of contact pad regions 212. For example, contact pad region 212a is electrically connected through metallization to the conductive electrode (not shown) on upper silicon layer 230, contact pad region 212b is electrically connected to electrodes 250, 251 of mass beam structure 231, and contact pad region 212c is electrically connected to conductive electrode 224 formed on lower silicon layer 234. One such silicon capacitive sensor is available and further described in information available from VTI Hamlin (Finland).

As assembled, accelerometer sensing element 200 as shown in FIG. 7 includes a first end 202 which is generally parallel to a second end 204. Longitudinal axis 120 extends between first end 202 and second end 204. The axis of sensitivity along which acceleration is sensed is generally represented by axis 122 which is perpendicular to longitudinal axis 120. The accelerometer sensing element 200 further includes a first principle surface 206 extending between first end 202 and second end 204. First principle surface 206 is generally parallel to longitudinal axis 120. Further, first principle surface 206 defines a plane substantially orthogonal to the axis of sensitivity 122.

Accelerometer sensing element 200 further includes a second principle surface 208 which is generally parallel to first principle surface 206. As such, second principle surface 208 is orthogonal to the axis of sensitivity 122. The second principle surface 208 extends between first end 202 and second end 204 of the accelerometer sensing element and is generally spaced a predetermined distance from the first principle surface 206.

Completing the generally rectangular configuration of the accelerometer sensing element 200 are first and second side surfaces 210, 211 which extend, respectively, between first end 202 and second end 204. Such side surfaces 210, 211 generally lie orthogonal to the first and second principle surfaces 206, 208.

As shown in FIG. 7, first end 202 which lies generally parallel to second end 204 includes conductive pad regions 212 (i.e., 212a–212c) and optionally conductive pad regions 213. Conductive pad regions 212a–212c (referred to collectively as conductive pad regions 212) are used for output of information signals from accelerometer sensing element 200. Conductive pad regions 213 are generally used for mechanical stability. For example, as shown with reference to first end 202, conductive pad regions 213, 212 are symmetrically distributed about longitudinal axis 120. As will be recognized by one skilled in the art from the description below with respect to attachment of first multilayer end cap 106 to the accelerometer sensing element 200, by distributing such conductive pad regions about axis 120, mechanical stability with regard to attachment of the end cap layer to the sensing element 200 is enhanced. For example, uneven stress between the multilayer end cap and the sensing element 200, which may occur if an asymmetrical distribution of conductive pad regions is used, is reduced. Likewise, second end 204 also includes conductive pad regions 212, 213 in a manner like those provided on first end 202.

As used herein, principle surface refers to a surface which is mounted adjacent to substrate 102 when the accelerometer device 100 is surface mounted thereon. As will be readily apparent from the description below, it is possible to mount accelerometer device 100 with first principle surface 206 directly adjacent the substrate 102 or second principle surface 208 directly adjacent the substrate 102. In other words, the device 100 can be mounted 1800 in two axis without loss of functionality.

Although the present invention is described herein with regard to an accelerometer sensing element, the mounting structure and configurations as described herein are also applicable to other types of force sensors or other sensors (transducers) which have a single axis of sensitivity. Further, accelerometers as described herein having a single axis of sensitivity may be conventional piezo electric accelerometers, piezo resistive accelerometers, or, for example, as described with reference to FIGS. 7–8, such accelerometers may be capacitive accelerometer sensing elements. As described above, the contact pad regions 212 would only permit for mounting of the accelerometer sensing element 200 with its axis of sensitivity 122 being parallel to a mounting plane defined by a substrate, e.g., printed circuit board. With use of the mounting structure according to the present invention, the accelerometer sensing element 200 may be surface mounted to a substrate 102 such that its axis of sensitivity 122 is rotated 90°, i.e., generally orthogonal to the mounting plane defined by the substrate 102.

The mounting structure according to the present invention provides for such rotation of the axis of sensitivity 122 relative to the mounting plane defined by the substrate 102 for sensing elements whose contact pad regions for providing information signals therefrom lie in a plane generally parallel to the axis of sensitivity, such as represented by the accelerometer sensing element 200 of FIG. 7. As shown in FIGS. 3–6, first and second multilayer end caps 106,108 provide for rotating the contact regions for mounting the accelerometer sensing element 200 such that they lie within a plane that lies generally orthogonal to the axis of sensitivity 122, e.g., surface mount contact regions 138 lie in a plane perpendicular to the axis of sensitivity 122, as opposed to being parallel to the axis of sensitivity, e.g., contact pad regions 212 lie in a plane parallel to the axis of sensitivity 122.

Figure 4:
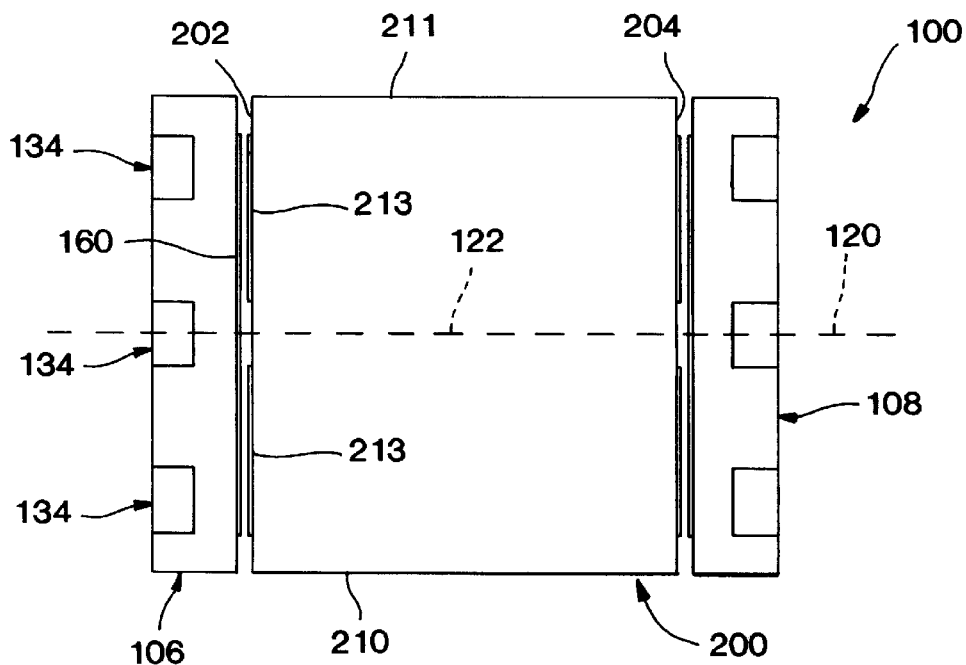
FIG. 4 is an exploded top view of the accelerometer device of FIG. 3.
Figure 5:
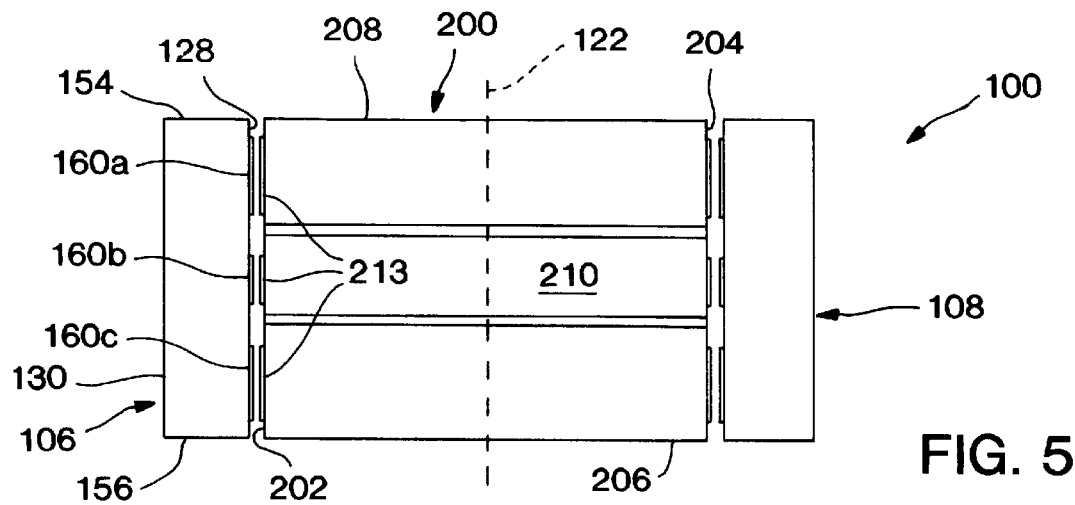
FIG. 5 is an exploded side view of the accelerometer device of FIG. 3.
Figure 6A:
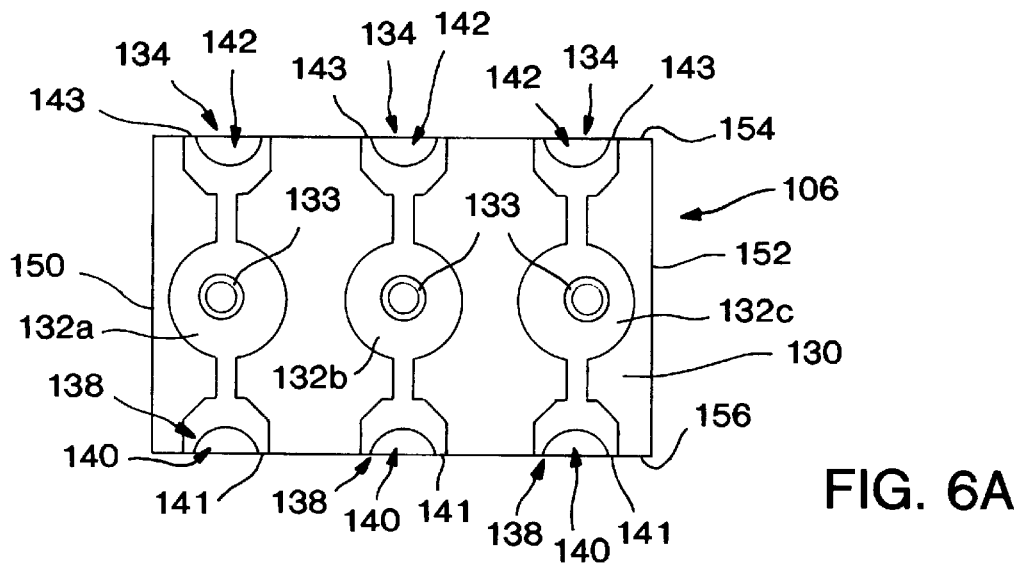
FIGS. 6A and 6B are front and rear views, respectively, of a multilayer end cap of the accelerometer device of FIG. 3.
Figure 6B:
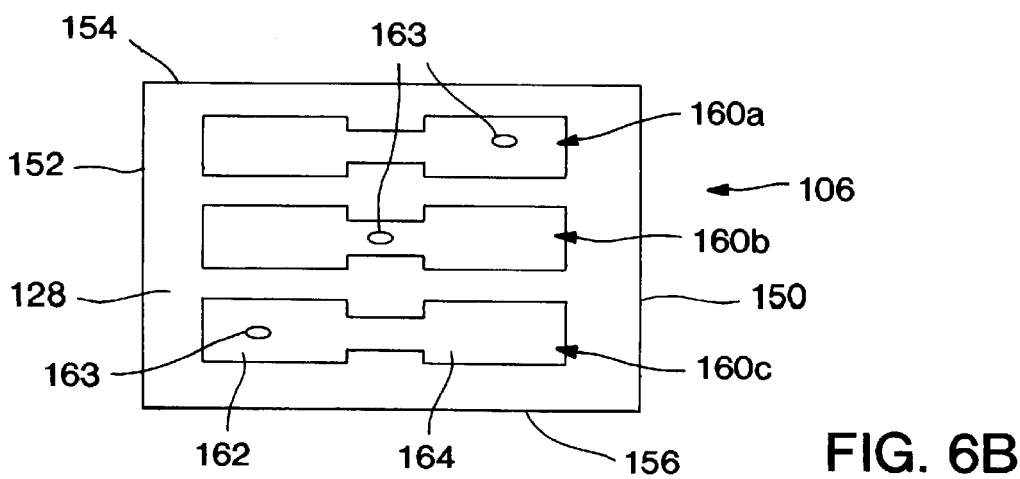

FIGS. 3–6 generally show details of the first and second multilayer end caps 106, 108 and the general attachment of such first and second multilayer end caps 106, 108 to accelerometer sensing element 200. FIG. 4 generally shows an exploded top view of the accelerometer device 100. FIG. 5 generally shows an exploded side view of the accelerometer device 100 shown in FIG. 3. Further, FIGS. 6A and 6B generally show front and rear views, respectively, of the multilayer end cap 106.

First and second multilayer end caps 106, 108 are substantially identical. Therefore, for simplicity, only first end cap 106 shall be described in detail herein. The first multilayer end cap 106. includes a first side 128 and a second side 130. Generally, first and second sides 128, 130 are parallel to one another and both extend between upper edge 154 and lower edge 156 of the first multilayer end cap 106. Further, multilayer end cap 106 includes first and second side edges 150, 152 which are generally orthogonal to upper and lower edges 154, 156 to form a generally rectangular end cap.

Each of the first and second multilayer end caps 106, 108 provide for an electrical path from the conductive pad regions 212, 213 of the accelerometer sensing element 200 to a terminating pad region for electrical connection to metallization on a substrate 102. The first and second end caps 106, 108 include metallization adequate to provide for such electrical paths and for attachment of the accelerometer sensing element 200 in an orientation rotated 90° from a conventional orientation using only the conductive pad regions 212, 213 of the accelerometer sensing element 200 alone.

As shown with regard to first multilayer end cap 106, metallization thereof includes conductive elements 160 on first side 128 of the first multilayer end cap 106. The conductive elements 160 which include conductive elements 160a–160c are sized and positioned for contact with conductive pad regions 212, 213 on first end 202 of accelerometer sensing element 200. The conductive elements 160a–160c, referred to herein collectively as conductive elements 160, are symmetrically distributed on first side 128 just as conductive pad regions 212, 213 are symmetrically distributed on first end 202 of the accelerometer sensing element 200. In this manner, the stresses on the attachment of the conductive elements 160 to conductive pad regions 212, 213 are reduced as forces resulting from attachment are distributed across the entire surface area of the first side 128 and the first end 202. Such forces would not be distributed across the entire surface if only conductive elements 160 associated with conductive pad regions 212 are used. Symmetrical distribution therefor results in a more mechanically stable part. Preferably, the conductive elements 160 are attached to conductive pad regions 212, 213 using solder, such as the commonly used 95SN/5SB solder. However, other methods of attachment, such as conductive adhesive, may also be used.

First multilayer end cap 106 further includes metallization also referred to herein as conductive traces 132 on the second side 130 thereof. Conductive traces 132 on second side 130 of the first multilayer end cap 106 provides for electrical connection to metallization on substrate 102. The conductive traces 132 are also electrically connected to the conductive elements 160 by a layer of metallization (not shown) between the first side 128 and second side 130 of the first multilayer end cap 106. This inner layer of metallization (not shown) provides for electrical connection of the conductive elements 160 to conductive traces 132. For example, conductive trace 132a is electrically connected to conductive element 160a, conductive trace 132b is electrically connected to conductive element 160b, and conductive trace 132c is electrically connected to conductive element 160c.

Vias 133 provide for electrical connection of the conductive traces 132 to the inner metallization layer (not shown).

Likewise, vias 163 provide for electrical connection of the conductive elements 160 to the inner metallization layer (not shown). As indicated previously, the inner metallization layer of the multilayer first end cap 106 provides for the appropriate connection of conductive elements 160 to conductive traces 132.

Preferably, the multilayer end caps 106, 108 include a first and second ceramic layer having an inner metallization layer sandwiched therebetween with the conductive elements 160 formed on a first side 128 thereof and the conductive traces 132 formed on the second side 130 thereof. However, various materials may be used to form the end caps. For example, materials which tend to match the thermal coefficient of expansion characteristics of the sensing element may be used to reduce thermal caused stresses between the components.

The conductive traces 132 extend to surface mount contact regions 138 along lower edge 156 and to surface contact regions 134 along upper edge 154 of the multilayer end cap 106. Each of the surface mount contact regions 138 along lower edge 156 include a conductive portion which lies in a plane defined by the first principle surface 206 of accelerometer sensing element 200 when the first multilayer end cap 106 is attached to the accelerometer sensing element 200. Likewise, surface mount contact regions 134 lying along upper edge 154 include portions thereof which lie in a plane defined by second principle surface 208 of the accelerometer sensing element 200.

Each of the surface mount contact regions 138 include a conductive lined opening 140 having a conductive opening edge 141. The conductive opening edge 141 is the portion of the surface mount contact region 138 which lies in the plane defined by the first principle surface 206 of the accelerometer sensing element 200 when the first multilayer end cap 106 is attached thereto. Likewise, each of surface mount contact regions 134 include a conductive lined opening 142 having a conductive opening edge 143 which lies in the plane defined by the second principle surface 208 of the accelerometer sensing element 200 when end cap 206 is attached thereto.

The use of multiple terminations through the extension of each conductive trace 132 to a surface mount contact region 138 along the lower edge 156 of the first multilayer end cap 106 and to a surface mount contact region 134 along the upper edge 154 of the first multilayer end cap 106 provides several advantages. First, the accelerometer device 100 may be mounted on substrate 102 using either surface mount contact regions 134 or surface mount contact regions 138 without any difference in functionality. This allows the accelerometer device 100 to be mounted 180° in two axes and still maintain functionality. In other words, the entire accelerometer device 100 can be flipped 180° from a mounting position wherein first principle surface 206 is adjacent substrate 102 to an orientation wherein second principle surface 208 is adjacent substrate 102.

Further, having multiple surface mount contact regions for each conductive trace 132 provides for a test point after the accelerometer device 100 is mounted on substrate 102. For example, if the accelerometer device 100 is mounted using surface mount contact regions 138, then surface mount contact regions 134 may be used for testing purposes.

Generally, the surface mount contact regions 138, 134 may include any number of different surface mount contact region configurations. For example, such regions may extend in a gull wing lead configuration. However, the conductive lined opening configuration as used herein provides advantages such as small package size, low hardware cost, ease of manufacturing, and ease of testability.

Although various methods may be used for mounting the accelerometer device 100, preferably, wet solder paste is stencil printed on conductive pads of a substrate upon which the device 100 is to be mounted. The surface mount contact regions of the accelerometer device 100 are then placed in contact with the wet solder paste on the conductive pads and then reflowed and cooled to form the interconnect desired.

The use of multilayer end caps, such as 106, 108, provides an efficient means of mass producing the accelerometer device 100. The first and second multilayer end caps 106, 108 may be produced in an array and then singulated to provide the individual first and second multilayer end caps 106, 108. Each of the end caps is substantially identical. The multilayer end caps may be fabricated using multiple layers of ceramic including an isolated inner metallization layer (not shown). However, as previously described, any suitable material may be used.

The use of the first and second multilayer end caps 106, 108 allow the accelerometer device 100 to be provided in a very small and compact package. Further, the number of mounting elements is kept to a minimum with electrical connections between the various elements also kept to a minimum. Overall, this packaging approach provides for a very robust accelerometer device 100. For example, the ceramic end caps protects the less durable silicon.

The preceding specific embodiments are illustrative of the practice of the invention. It is to be understood, therefore, that other expedients known to those skilled in the art or disclosed herein may be employed without departing from the invention or the scope of the attached claims. For example, the present invention is not limited to the use of certain materials as described herein and is not limited to the use of multilayer end caps with only accelerometer sensor elements but may be used with other transducing elements having a single axis of sensitivity. Further, the device may be provided with multiple terminations from the conductive traces as described herein or terminations extending along only one edge of the end cap. The present invention is also not limited to use in connection with medical apparatus, but may find further application in other areas such as automobile applications. The present invention further includes within its scope methods of making and using the accelerometer device according to the present invention and methods of making and using assemblies thereof.

What is claimed is:

1. A method for providing a medical device including an accelerometer, the method comprising the steps of:

providing a medical device having a housing;

providing a substrate, the substrate defining a mounting plane and including two or more surface mount contact pads;

providing an accelerometer device to be mounted on the substrate, wherein providing the accelerometer device includes:

providing an accelerometer sensing element having an axis of sensitivity, wherein the accelerometer sensing element includes a device body having a longitudinal axis extending between generally parallel first and second ends thereof, wherein the accelerometer device further has a first principal surface extending between the first and second ends of the device body parallel to the longitudinal axis, wherein the axis of sensitivity is perpendicular to a plane defined by the first principal surface, and further wherein the accelerometer sensing element includes two or more conductive pad regions on each of the first and second ends of the device body, providing a first and a second multilayer end cap, wherein each of the first and second multilayer end caps includes two or more conductive elements on one side thereof and further includes two or more conductive traces electrically connected to the two or more conductive elements thereof, each of the two or more conductive traces of each of the first and second multilayer end caps terminating at a surface mount contact regions along at least one edge thereof, and attaching the first and second multilayer end caps to the first and second ends of the device body, respectively, with the conductive elements of the first and second multilayer end caps in electrical contact with the conductive pad regions of the first and second ends of the device body;

mounting the accelerometer device on the substrate with the surface mount contact regions electrically connected to the two or more surface mount contact pads of the substrate such that the axis of sensitivity of the accelerometer sensing element is perpendicular to the mounting plane defined by the substrate; and enclosing the substrate having the accelerometer device mounted thereon in the housing of the medical device.

2. The method of claim 1, wherein providing the first and second multilayer end caps includes the step of providing first and second multilayer end caps which each include generally parallel first and second sides extending between first and second edges thereof, wherein at least one of the first and second edges of the multilayer end cap lies in the plane defined by the first principal surface, wherein the first side of each of the first and second multilayer end caps includes the two or more conductive elements for electrical connection to the two or more conductive pad regions on each of the first and second ends of the device body, respectively, wherein the second side of each of the multilayer end caps includes the two or more conductive traces with each conductive trace electrically connected to at least one conductive element on the first side thereof, and further wherein each of the two or more conductive traces on the second side of each of the first and second multilayer end caps terminates in the surface mount contact region along the at least one of the first and second edges lying in the plane defined by the first principal surface.

3. The method of claim 1, wherein the device body includes a second principal surface extending between the first and second ends thereof generally parallel to the principal surface, wherein the axis of sensitivity is perpendicular to a plane defined by the second principal surface, and further wherein each of the two or more conductive traces of each of the first and second multilayer end caps terminate in a surface mount contact region along the first edge of the respective multilayer end cap lying in the plane defined by the principal surface and a surface mount contact region along the second edge of the respective multilayer end cap lying in the plane defined by the second principal surface.

4. The method of claim 1, wherein the accelerometer sensing element is a capacitive sensing element with one or more electrodes lying in corresponding planes generally parallel to the principal surface and perpendicular to the axis of sensitivity.

5. The method of claim 1, wherein the two or more conductive pads on each of the first and second ends of the device body of the accelerometer sensing element are symmetrically distributed relative to the longitudinal axis, and further wherein the two or more conductive elements on the first side of each of the first and second multilayer end caps are positioned for electrical contact with the symmetrically distributed conductive pad regions.

6. The method of claim 1, wherein each surface mount contact region along the at least one edge includes a conductive lined opening having a conductive opening edge lying in the plane defined by the principal surface.

7. The method of claim 1, wherein providing the medical device includes providing a medical device selected from one of a pacemaker, a defibrillator, a brain stimulator, a cardioverter/defibrillator, a pacemaker/cardioverter/defibrillator, a neurostimulator, a muscle stimulator, a gastric stimulator, an implantable monitor, a hemodynamic monitor, and a drug pump.

8. A surface mountable accelerometer device for use in an implantable medical apparatus, the surface mountable accelerometer comprising:

an accelerometer sensing element having an axis of sensitivity, wherein the accelerometer sensing element comprises a device body having a longitudinal axis extending between generally parallel first and second ends thereof, wherein the accelerometer device further has a first principal surface extending between the first and second ends of the device body parallel to the longitudinal axis, wherein the axis of sensitivity is perpendicular to a plane defined by the first principal surface, and further wherein the accelerometer sensing element includes two or more conductive pad regions on each of the first and second ends of the device body; and a first and a second multilayer end caps, the first multilayer end cap connected to the first end of the device body and the second multilayer end cap connected to the second end of the device body, wherein each of the first and second multilayer end caps includes generally parallel first and second sides extending between first and second edges thereof, wherein at least one of the first and second edges of the multilayer end cap lies in the plane defined by the first principal surface, wherein the first side of each of the first and second multilayer end caps includes two or more conductive elements for electrical connection to the two or more conductive pad regions on each of the first and second ends of the device body, respectively, wherein the second side of each of the multilayer end caps includes two or more conductive traces with each conductive trace electrically connected to at least one conductive element on the first side thereof, and further wherein each of the two or more conductive traces on the second side of each of the first and second multilayer end caps terminates in a surface mount contact region along the at least one of the first and second edges lying in the plane defined by the first principal surface.

9. The device of claim 8, wherein the device body includes a second principal surface extending between the first and second ends thereof generally parallel to the first principal surface, wherein the axis of sensitivity is perpendicular to a plane defined by the second principal surface, and further wherein each of the two or more conductive traces on the second side of each of the first and second multilayer end caps terminate in a surface mount contact region along the first edge of the respective multilayer end cap lying in the plane defined by the first principal surface and a surface mount contact region along the second edge of the respective multilayer end cap lying in the plane defined by the second principal surface.

10. The device of claim 8, wherein the accelerometer sensing element is a capacitive sensing element with one or more electrodes lying in corresponding planes generally parallel to the first principal surface and perpendicular to the axis of sensitivity.

11. The device of claim 8, wherein the two or more conductive pad regions on each of the first and second ends of the device body of the accelerometer sensing element are symmetrically distributed relative to the longitudinal axis, and further wherein the two or more conductive elements on the first side of each of the first and second multilayer end caps are positioned for electrical contact with the symmetrically distributed conductive pad regions.

12. The device of claim 8, wherein each of the surface mount contact regions along the at least one of the first and second edges lying in the plane defined by the first principal surface includes a conductive lined opening having a conductive opening edge lying in the plane defined by the first principal surface.

13. The device of claim 8, wherein the medical apparatus is selected from one of a pacemaker, a defibrillator, a cardioverter/defibrillator, a pacemaker/cardioverter/defibrillator, a brain stimulator, a neurostimulator, a muscle stimulator, a gastric stimulator, an implantable monitor, a hemodynamic monitor, and a drug pump, and further wherein the accelerometer device is hermetically sealed in the medical apparatus.

14. A surface mountable accelerometer device, comprising:
   an accelerometer sensing element having an axis of sensitivity, wherein the accelerometer sensing element includes a device body having a longitudinal axis extending between generally parallel first and second ends thereof, wherein the accelerometer sensing element further has at least a first principal surface extending between the first and second ends of the device body parallel to the longitudinal axis, wherein the axis of sensitivity is perpendicular to a plane defined by the first principal surface, and further wherein the accelerometer sensing element includes two or more conductive pad regions on at least one of the first and second ends of the device body; and
   at least one multilayer end cap connected to at least one of the first and second ends of the device body, wherein the at least one multilayer end cap includes generally parallel first and second sides extending between first and second edges of the multilayer end cap, wherein at least one of the first and second edges of the at least one multilayer end cap lies in the plane defined by the first principal surface, wherein the first side of the multilayer end cap includes two or more conductive elements for electrical connection to the two or more conductive pad regions on the at least one of the first and second ends of the device body, wherein the second side of the at least one multilayer end cap includes two or more conductive traces with each conductive trace electrically connected to at least one conductive element on the first side of the at least one multilayer end cap, and further wherein each conductive trace on the second side of the at least one multilayer end cap terminates in a surface mount contact region along the at least one of the first and second edges lying in the plane defined by the first principal surface.

15. The device of claim 14, wherein the at least one multilayer end cap includes a first and a second multilayer end cap, the first multilayer end cap connected to the first end of the device body and the second multilayer end cap connected to the second end of the device body, wherein each of the first and second multilayer end caps includes generally parallel first and second sides extending between first and second edges thereof, wherein at least one of the first and second edges of the first and second multilayer end caps lies in the plane defined by the principal surface, wherein the first side of each of the first and second multilayer end caps includes two or more conductive elements for electrical connection to two or more conductive pad regions on each of the first and second ends of the device body, respectively, wherein the second side of each of the multilayer end caps includes two or more conductive traces with each conductive trace electrically connected to at least one conductive element on the first side thereof, and further wherein each of the two or more conductive traces on the second side of each of the first and second multilayer end caps terminates in a surface mount contact region along the at least one of the first and second edges lying in the plane defined by the principal surface.

16. The device of claim 15, wherein the device body includes a second principal surface extending between the first and second ends thereof generally parallel to the first principal surface, wherein the axis of sensitivity is perpendicular to a plane defined by the second principal surface, and further wherein each of the two or more conductive traces on the second side of each of the first and second multilayer end caps terminate in a surface mount contact region along the first edge of the respective multilayer end cap lying in the plane defined by the first principal surface and a surface mount contact region along the second edge of the respective multilayer end cap lying in the plane defined by the second principal surface.

17. The device of claim 15, wherein the two or more conductive pad regions on each of the first and second ends of the device body of the accelerometer sensing element are symmetrically distributed relative to the longitudinal axis, and further wherein the two or more conductive elements on the first side of each of the first and second multilayer end caps are positioned for electrical contact with the symmetrically distributed conductive pad regions.

18. The device of claim 14, wherein the accelerometer sensing element is a capacitive sensing element with one or more electrodes lying in corresponding planes generally parallel to the first principal surface and perpendicular to the axis of sensitivity.

19. The device of claim 14, wherein each of the surface mount contact regions along the at least one of the first and second edges lying in the plane defined by the first principal surface includes a conductive lined opening having a conductive opening edge lying in the plane defined by the first principal surface.

20. An accelerometer assembly for use in a medical device, the accelerometer assembly comprising:
   a substrate defining a mounting plane, the substrate including two or more surface mount contact pads;
   an accelerometer sensing element having an axis of sensitivity mounted on the substrate, wherein the accelerometer sensing element includes a device body having a longitudinal axis extending between generally parallel first and second ends thereof, wherein the accelerometer assembly further has a first principal surface extending between the first and second ends of the device body parallel to the longitudinal axis and to the mounting plane of the substrate, wherein the axis of sensitivity is perpendicular to a plane defined by the first principal surface, and further wherein the accelerometer sensing element includes two or more conductive pad regions on each of the first and second ends of the device body; and a first and a second multilayer end cap, the first multilayer end cap connected to the first end of the device body and the second multilayer end cap connected to the second end of the device body, wherein each of the first and second multilayer end caps includes two or more conductive elements on one side thereof for electrical connection to the two or more conductive pad regions on each of the first and second ends of the device body, respectively, and further wherein each of the first and second multilayer end caps includes two or more conductive traces electrically connected to the two or more conductive elements thereof, each of the two or more conductive traces of each of the first and second multilayer end caps terminating at a surface mount contact region along at least one edge thereof, and further wherein the surface mount contact regions are electrically connected to the two or more surface mount contact pads of the substrate such that the axis of sensitivity of the accelerometer sensing element is perpendicular to the mounting plane defined by the substrate.

21. The assembly of claim 20, wherein each of the first and second multilayer end caps includes generally parallel first and second sides extending between first and second edges thereof, wherein at least one of the first and second edges of the multilayer end caps lies in the plane defined by the first principal surface, wherein the first side of each of the first and second multilayer end caps includes the two or more conductive elements for electrical connection to the two or more conductive pad regions on each of the first and second ends of the device body, respectively, wherein the second side of each of the multilayer end caps includes the two or more conductive traces with each conductive trace electrically connected to at least one conductive element on the first side thereof, and further wherein each of the two or more conductive traces on the second side of each of the first and second multilayer end caps terminates in the surface mount contact region along the at least one of the first and second edges lying in the plane defined by the first principal surface.

22. The assembly of claim 21, wherein the device body includes a second principal surface extending between the first and second ends thereof generally parallel to the first principal surface, wherein the axis of sensitivity is perpendicular to a plane defined by the second principal surface, and further wherein each of the two or more conductive traces on the second side of each of the first and second multilayer end caps terminate in a surface mount contact region along the first edge of the respective multilayer end cap lying in the plane defined by the first principal surface and a surface mount contact region along the second edge of the respective multilayer end cap lying in the plane defined by the second principal surface.

23. The assembly of claim 20, wherein the accelerometer sensing element is a capacitive sensing element with one or more electrodes lying in corresponding planes generally parallel to the first principal surface and perpendicular to the axis of sensitivity.

24. The assembly of claim 20, wherein the two or more conductive pad regions on each of the first and second ends of the device body of the accelerometer sensing element are symmetrically distributed relative to the longitudinal axis, and further wherein the two or more conductive elements on the first side of each of the first and second multilayer end caps are positioned for electrical contact with the symmetrically distributed conductive pad regions.

25. The assembly of claim 20, wherein each of the surface mount contact regions along the at least one edge includes a conductive lined opening having a conductive opening edge lying in the plane defined by the first principal surface.

26. The assembly of claim 20, wherein the medical device is selected from one of a pacemaker, a defibrillator, a cardioverter/defibrillator, a pacemaker/cardioverter/defibrillator, a brain stimulator, a neurostimulator, a muscle stimulator, a gastric stimulator, an implantable monitor, a hemodynamic monitor, and a drug pump, and further wherein the accelerometer assembly is enclosed in the medical device.

27. A transducer assembly comprising:

a substrate defining a mounting plane, the substrate including two or more surface mount contact pads;

a sensing element having an axis of sensitivity, wherein the sensing element includes a device body having a longitudinal axis extending between first and second ends thereof, wherein the sensing element further has a first principal surface extending between the first and second ends of the device body parallel to the longitudinal axis and to the mounting plane of the substrate, wherein the axis of sensitivity is perpendicular to a plane defined by the first principal surface, and further wherein the sensing element includes two or more conductive pad regions on at least one of the first and second ends of the device body; and at least one interposer element connected to at least one of the first and second ends of the device body, wherein the at least one interposer element includes two or more conductive elements along one side thereof for electrical connection to the two or more conductive pad regions on the at least one of the first and second ends of the device body and two or more surface mount contact regions along an edge thereof electrically connected to the two or more conductive elements, each of the two or more surface mount contact regions electrically connected to the two or more surface mount contact pads of the substrate such that the axis of sensitivity of the accelerometer sensing element is perpendicular to the mounting plane defined by the substrate.

28. The assembly of claim 27, wherein the at least one interposer element includes a first and second multilayer end cap, the first multilayer end cap connected to the first end of the device body and the second multilayer end cap connected to the second end of the device body, wherein each of the first and second multilayer end caps includes two or more conductive elements on one side thereof for electrical connection to two or more conductive pad regions on each of the first and second ends of the device body, respectively, and further wherein each of the first and second multilayer end caps includes two or more conductive traces electrically connected to the two or more conductive elements thereof, each of the two or more conductive races of each of the first and second multilayer end caps terminating at a surface mount contact region along at least one edge thereof, and further wherein the surface mount contact regions are electrically connected to the two or more surface mount contact pads of the substrate such that the axis of sensitivity of the accelerometer sensing element is perpendicular to the mounting plane defined by the substrate.

29. The assembly of claim 28, wherein each of the first and second multilayer end caps include generally parallel first and second sides extending between first and second edges thereof, wherein at least one of the first and second edges of the multilayer end caps lies in the plane defined by the principal surface, wherein the first side of each of the first and second multilayer end caps includes the two or more conductive elements for electrical connection to the two or more conductive pad regions on each of the first and second ends of the device body, respectively, wherein the second side of each of the multilayer end caps includes the two or more conductive traces with each conductive trace electrically connected to at least one conductive element on the first side thereof, and further wherein each of the two or more conductive traces on the second side of each of the first and second multilayer end caps terminates in the surface mount contact region along the at least one of the first and second edges lying in the plane defined by the first principal surface.

30. The assembly of claim 28, wherein the device body includes a second principal surface extending between the first and second ends thereof generally parallel to the first principal surface, wherein the axis of sensitivity is perpendicular to a plane defined by the second principal surface, and further wherein each of the two or more conductive traces on the second side of each of the first and second multilayer end caps terminate in a surface mount contact region along the first edge of the respective multilayer end cap lying in the plane defined by the first principal surface and a surface mount contact region along the second edge of the respective multilayer end cap lying in the plane defined by the second principal surface.

31. The assembly of claim 27, wherein the sensing element is an accelerometer sensing element.

32. The assembly of claim 31, wherein the accelerometer sensing element is a capacitive sensing element with one or more electrodes lying in corresponding planes generally parallel to the first principal surface and perpendicular to the axis of sensitivity.

33. The assembly of claim 27, wherein the two or more conductive pad regions on each of the first and second ends of the device body of the sensing element are symmetrically distributed relative to the longitudinal axis, and further wherein the two or more conductive elements of the at least one interposer element are positioned for electrical contact with the symmetrically distributed conductive pad regions.

34. The assembly of claim 27, wherein each of the surface mount contact regions includes a portion lying along the plane defined by the first principal surface.

35. The assembly of claim 34, wherein each of the surface mount contact regions includes a conductive lined opening having a conductive opening edge lying in the plane defined by the first principal surface.

36. A method of providing a transducer assembly, the method comprising the steps of:
providing a substrate defining a mounting plane, the substrate including two or more surface mount contact pads;
providing a transducer device, wherein providing the transducer device includes the steps of:
providing a sensing element having an axis of sensitivity, wherein the sensing element includes a device body having a longitudinal axis extending between first and second ends thereof, wherein the sensing element further includes a first principal surface extending between the first and second ends of the device body parallel to the longitudinal axis, wherein the axis of sensitivity is perpendicular to a plane defined by the first principal surface, and further wherein the sensing element includes two or more conductive pad regions on at least one of the first and second ends of the device body,
providing at least one interposer element, wherein the at least one interposer element includes two or more conductive elements along one side thereof and further includes two or more surface mount contact regions along an edge thereof electrically connected to the two or more conductive elements,
attaching the at least one interposer element to at least one of the first and second ends of the device body with the conductive elements of the at least one interposer element in electrical contact with the conductive pad regions on at least one of the first and second ends of the device body;
mounting the transducer device on the substrate with the two or more surface mount contact regions electrically connected to the two or more surface mount contact pads of the substrate such that the axis of sensitivity of the sensing element is perpendicular to the mounting plane defined by the substrate.

37. The method of claim 36, wherein the at least one interposer element includes a first and a second multilayer end cap, the first multilayer end cap connected to the first end of the device body and the second multilayer end cap connected to the second end of the device body, wherein each of the first and second multilayer end caps includes two or more conductive elements on one side thereof for electrical connection to the two or more conductive pad regions on each of the first and second ends of the device body, respectively, wherein each of the first and second multilayer end caps includes two or more conductive traces electrically connected to the two or more conductive elements thereof, each of the two or more conductive traces of each of the first and second multilayer end caps terminating at a surface mount contact region along at least one edge thereof, and further wherein the surface mount contact regions are electrically connected to the two or more surface mount contact pads of the substrate such that the axis of sensitivity of the sensing element is perpendicular to the mounting plane defined by the substrate.

38. The method of claim 37, where each of the first and second multilayer end caps includes generally parallel first and second sides extending between first and second edges thereof, wherein at least one of the first and second edges of the first and second multilayer end caps lies in the plane defined by the principal surface, wherein the first side of each of the first and second multilayer end caps includes the two or more conductive elements for electrical connection to the two or more conductive pad regions on each of the first and second ends of the device body, respectively, wherein the second side of each of the multilayer end caps includes the two or more conductive traces with each conductive trace electrically connected to at least one conductive element on the first side thereof, and further wherein each of the two or more conductive traces on the second side of each of the first and second multilayer end caps terminates in the surface mount contact region along the at least one of the first and second edges lying in the plane defined by the first principal surface.

39. The method of claim 38, wherein the device body includes a second principal surface extending between the first and second ends thereof generally parallel to the first principal surface, wherein the axis of sensitivity is perpendicular to a plane defined by the second principal surface, and further wherein each of the two or more conductive traces on the second side of each of the first and second multilayer end caps terminate in a surface mount contact region along the first edge of the respective multilayer end cap lying in the plane defined by the first principal surface and a surface mount contact region along the second edge of the respective multilayer end cap lying in the plane defined by the second principal surface.

40. The method of claim 36, wherein the sensing element is an accelerometer sensing element.

41. The method of claim 40, wherein the accelerometer sensing element is a capacitive sensing element with one or more electrodes lying in corresponding planes generally parallel to the first principal surface and perpendicular to the axis of sensitivity.

42. The method of claim 36, wherein the two or more conductive pad regions on each of the first and second ends of the device body of the sensing element are symmetrically distributed relative to the longitudinal axis, and further wherein the two or more conductive elements of the at least one interposer element are positioned for electrical contact with the symmetrically distributed conductive pad regions.

43. The method of claim 36, wherein each of the surface mount contact regions includes a portion lying along the plane defined by the first principal surface.

44. The method of claim 43, wherein each of the surface mount contact regions includes a conductive lined opening having a conductive opening edge lying in the plane defined by the first principal surface.

45. A method for providing an accelerometer device for use in a medical device, the method comprising the steps of:
  providing an accelerometer sensing element having an axis of sensitivity, wherein the accelerometer sensing element includes a device body having a longitudinal axis extending between generally parallel first and second ends thereof, wherein the accelerometer sensing element further includes a first principal surface extending between the first and second ends of the device body parallel to the longitudinal axis, wherein the axis of sensitivity is perpendicular to a plane defined by the first principal surface, and further wherein the accelerometer sensing element includes two or more conductive pad regions on each of the first and second ends of the device body;
  providing a first and a second multilayer end cap, wherein each of the first and second multilayer end caps includes two or more conductive elements on one side thereof and further includes two or more conductive traces electrically connected to the two or more conductive elements thereof, each of the two or more conductive traces of each of the first and second multilayer end caps terminating at a surface mount contact region along at least one edge thereof; and
  attaching the first and second multilayer end caps to the first and second ends of the device body, respectively, the conductive elements of the first and second multilayer end caps in electrical contact with the conductive pad regions of the respective first and second ends of the device body.

46. The method of claim 45, wherein each of the first and second multilayer end caps includes generally parallel first and second sides extending between first and second edges thereof, wherein at least one of the first and second edges of the first and second multilayer end caps lies in the plane defined by the first principal surface, wherein the first side of each of the first and second multilayer end caps includes the two or more conductive elements for electrical connection to the two or more conductive pad regions on each of the first and second ends of the device body, respectively, wherein the second side of each of the multilayer end caps includes the two or more conductive traces with each conductive trace electrically connected to at least one conductive element on the first side thereof, and further wherein each of the two or more conductive traces on the second side of each of the first and second multilayer end caps terminates in a surface mount contact region along the at least one of the first and second edges lying in the plane defined by the first principal surface.

47. The method of claim 46, wherein the device body includes a second principal surface extending between the first and second ends thereof generally parallel to the first principal surface, wherein the axis of sensitivity is perpendicular to a plane defined by the second principal surface, and further wherein each of the two or more conductive traces on the second side of each of the first and second multilayer end caps terminate in a surface mount contact region along the first edge of the respective multilayer end cap lying in the plane defined by the first principal surface and a surface mount contact region along the second edge of the respective multilayer end cap lying in the plane defined by the second principal surface.

48. The method of claim 45, wherein the accelerometer sensing element is a capacitive sensing element with one or more electrodes lying in corresponding planes generally parallel to the first principal surface and perpendicular to the axis of sensitivity.

49. The method of claim 45, wherein the two or more conductive pad regions on each of the first and second ends of the device body of the accelerometer sensing element are symmetrically distributed relative to the longitudinal axis, and further wherein the two or more conductive elements on the first side of each of the first and second multilayer end caps are positioned for electrical contact with the symmetrically distributed conductive pad regions.

50. The method of claim 45, wherein each of the surface mount contact regions along the at least one edge includes a conductive lined opening having a conductive opening edge lying in the plane defined by the first principal surface.

51. The method of claim 45, wherein the medical device includes a medical device selected from one of a pacemaker, a defibrillator, a brain stimulator, a cardioverter/defibrillator, a neurostimulator, a muscle stimulator, a pacemaker/cardioverter/defibrillator, a gastric stimulator, an implantable monitor, a hemodynamic monitor, and a drug pump, and further wherein the method includes enclosing the accelerometer device within a housing of the medical device.

52. A method of providing a transducer device, the method comprising the steps of:
  providing a sensing element having an axis of sensitivity, wherein the sensing element includes a device body having a longitudinal axis extending between first and second ends thereof, wherein the sensing element further includes a first principal surface extending between the first and second ends of the device body parallel to the longitudinal axis, wherein the axis of sensitivity is perpendicular to a plane defined by the first principal surface, and further wherein the sensing element includes two or more conductive pad regions on at least one of the first and second ends of the device body;
  providing at least one interposer element, wherein the at least one interposer element includes two or more conductive elements along one side thereof and two or more surface mount contact regions along an edge thereof electrically connected to the two or more conductive elements; and
  attaching the at least one interposer element to at least one of the first and second ends of the device body with the conductive elements of the at least one interposer element in electrical contact with the conductive pad regions of one of the first and second ends of the device body.

53. The method of claim 52, wherein the at least one interposer element includes a first and second multilayer end cap, the first multilayer end cap connected to the first end of the device body and the second multilayer end cap connected to the second end of the device body, wherein each of the first and second multilayer end caps includes two or more conductive elements on one side thereof for electrical connection to the two or more conductive pad regions on each of the first and second ends of the device body, respectively, and further wherein each of the first and second multilayer end caps includes two or more conductive traces electrically connected to the two or more conductive elements thereof, each of the two or more conductive traces of each of the first and second multilayer end caps terminating at a surface mount contact region along at least one edge thereof.

54. The method of claim 53, where each of the first and second multilayer end caps includes generally parallel first and second sides extending between first and second edges thereof, wherein at least one of the first and second edges of the multilayer end cap lies in the plane defined by the first principal surface, wherein the first side of each of the first and second multilayer end caps includes the two or more conductive elements for electrical connection to the two or more conductive pad regions on each of the first and second ends of the device body, respectively, wherein the second side of each of the multilayer end caps includes the two or more conductive traces with each conductive trace electrically connected to at least one conductive element on the first side thereof, and further wherein each of the two or more conductive traces on the second side of each of the first and second multilayer end caps terminates in a surface mount contact region along the at least one of the first and second edges lying in the plane defined by the first principal surface.

55. The method of claim 54, wherein the device body includes a second principal surface extending between the first and second ends thereof generally parallel to the first principal surface, wherein the axis of sensitivity is perpendicular to a plane defined by the second principal surface, and further wherein each of the two or more conductive traces on the second side of each of the first and second multilayer end caps terminate in a surface mount contact region along the first edge of the respective multilayer end cap lying in the plane defined by the first principal surface and a surface mount contact region along the second edge of the respective multilayer end cap lying in the plane defined by the second principal surface.

56. The method of claim 53, wherein the sensing element is an accelerometer sensing element.

57. The method of claim 56, wherein the accelerometer sensing element is a capacitive sensing element with one or more electrodes lying in corresponding planes generally parallel to the first principal surface and perpendicular to the axis of sensitivity.

58. The method of claim 53, wherein the two or more conductive pad regions on the at least one of the first and second ends of the device body of the sensing element are symmetrically distributed relative to the longitudinal axis, and further wherein the two or more conductive elements of the at least one interposer element are positioned for electrical contact with the symmetrically distributed conductive pad regions.

59. The method of claim 53, wherein each of the surface mount contact regions includes a portion lying along the plane defined by the first principal surface.

60. The method of claim 59, wherein each of the surface mount contact regions includes a conductive lined opening having a conductive opening edge lying in the plane defined by the first principal surface.

* * * * *